(12) United States Patent
Arkles et al.

(10) Patent No.: US 6,410,770 B2
(45) Date of Patent: Jun. 25, 2002

(54) CHLORIDE-FREE PROCESS FOR THE PRODUCTION OF ALKYLSILANES SUITABLE FOR MICROELECTRONIC APPLICATIONS

(75) Inventors: Barry C. Arkles, Dresher; Youlin Pan, Langhorne; Gerald Larson, Newtown, all of PA (US)

(73) Assignee: Gelest, Inc., Tullytown, PA (US)

( * ) Notice: Subject to any disclaimer, the term of this patent is extended or adjusted under 35 U.S.C. 154(b) by 0 days.

(21) Appl. No.: 09/779,025

(22) Filed: Feb. 7, 2001

Related U.S. Application Data
(60) Provisional application No. 60/181,140, filed on Feb. 8, 2000.

(51) Int. Cl.$^7$ .................................................. C07F 7/08
(52) U.S. Cl. ........................ 556/466; 556/478; 556/487
(58) Field of Search ................................ 556/478, 466, 556/487

(56) References Cited

U.S. PATENT DOCUMENTS

| | | | |
|---|---|---|---|
| 4,774,347 A | * 9/1988 | Marko et al. ................ 556/466 |
| 6,054,379 A | 4/2000 | Yau et al. |
| 6,072,227 A | 6/2000 | Yau et al. |
| 6,147,009 A | 11/2000 | Grill et al. |
| 6,150,551 A | * 11/2000 | Kropfgans et al. ...... 556/466 X |
| 6,168,726 B1 | 1/2001 | Li et al. |
| 6,177,584 B1 | 1/2001 | Loewenberg et al. |
| 6,258,971 B1 | * 7/2001 | Schattenmann ............. 556/478 |

FOREIGN PATENT DOCUMENTS

| | | |
|---|---|---|
| EP | 0774533 | 5/1997 |
| EP | 1050600 | 11/2000 |
| WO | WO 99/48812 | 9/1999 |

OTHER PUBLICATIONS

Lein and Potzinger, "Oxidation of Trimethylsilyl Radicals by $N_2O$: A Mechanistic Study", *Organometallics*, vol. 19, No. 23, pp. 4701–4714 (2000).

N. Hendricks, et al., "Synthesizing Low–k CVD Materials for Fab Use", *Proc. of the 6$^{th}$ International Dielectrics for ULSI Multilevel Interconnection Conference*, pp. 1–7 (2000).

Loboda, et al., "Deposition of Low–K Dielectric Films Using Trimethylsilane", *Fall Mtg. of the Electrochemical Society Preprint* (1998).

Wlodarska, et al., "Electrical Properties of some Plasma Polymers Obtained by Remote Microwave Plasma Chemical Vapor Deposition", *SPIE–International Society for Optical Engineering* (1999) (Abstract Only).

Sundermeyer, et al., "Synthesis of Silanes in Molten Chloroaluminates", http://iusti.univ.–mrs.fr/EUCHEM98/abstract_euchem/sundermeyer.html (1998).

* cited by examiner

*Primary Examiner*—Paul F. Shaver
(74) *Attorney, Agent, or Firm*—Akin, Gump, Strauss, Hauer & Feld, L.L.P.

(57) ABSTRACT

This invention includes a process for producing an alkylsilane, comprising reducing an alkoxysilane in the presence of an alkali metal hydride in the presence of a high boiling solvent. The alkylsilane has a boiling point lower than the boiling point of the solvent, which is typically diglyme. This invention also includes a chloride-free alkylsilane formed from the reduction of an alkoxysilane in the presence of an alkali metal hydride. The alkylsilane produced according to the process of the present invention may be useful in microelectronic applications, such as in the production of chloride-free low dielectric constant materials which may be produced by the chemical vapor deposition of such silanes.

15 Claims, No Drawings

CHLORIDE-FREE PROCESS FOR THE PRODUCTION OF ALKYLSILANES SUITABLE FOR MICROELECTRONIC APPLICATIONS

CROSS-REFERENCE TO RELATED APPLICATION

This application claims the benefit of U.S. Provisional Application No. 60/181,140, filed Feb. 8, 2000.

BACKGROUND OF THE INVENTION

Trimethylsilane and other methylhydridosilanes are utilized as precursors for chemical vapor deposition (CVD) of low dielectric constant silicon dioxide-rich films in a variety of process protocols. These films are sometimes referred to as "carbon doped silicon dioxide" and "hydrogenated oxidized silicon carbon." Such low dielectric constant ("low-k") films, which also exhibit thermal stability, may be useful in advanced semiconductor integrated circuit technology. Although the method of deposition is not a subject of this patent, a discussion of the technology is useful in understanding the critical nature of precursor purity for the technology.

In the CVD process, the trimethylsilane or methylhydridosilane precursor is introduced into a deposition chamber containing the substrate in the presence of an oxidizing ambient. At elevated substrate temperatures (typically greater than about 300° C.), $N_2O$ and $O_2$ are used in a plasma assisted oxidation of the trimethylsilane, and the process is known as plasma enhanced CVD (PECVD).

The first step in the oxidation of the silane precursors is thought to be the conversion of the hydride substitution to an oxygen substitution, either by direct oxidation of the silyl hydride or through a trimethylsilyl radical intermediate. A mechanistic study, which examines the oxidation of trimethylsilyl radicals by $N_2O$, has been reported by Lein and Potzinger (*Organometallics*, 19, 4701, 2000). The second step is the further oxidation of the silane, resulting in removal of the methyl groups and the formation of films dominated by O—Si—O bonds, with some Si-C bonds maintained.

The resulting films thus contain a silicon-oxygen network that is interrupted by organic groups such as methyl. It has been shown (N. Hendricks, Proc. Of the $6^{th}$ International Dielectrics for ULSI Multilevel Interconnection Conference (DUMIC), Santa Clara, Calif., February 2000, p. 17), that the incorporation of methyl or other organic groups into the silicon-oxygen network has a significant effect on the thermal, physical, and chemical properties of the films. For example, the films exhibit reduced densities relative to silicon dioxide, resulting in lower dielectric constants. Typically, low dielectric constant films contain about 3 to 20 atom % carbon (atom % carbon=C/(C+Si+O)).

An example of a nitrous oxide PECVD method is provided by Loboda, et al. (1998 Fall Mtg Electrochemical Society Preprint). Using such a process, films containing a random network of C—Si—C and O—Si—O bonds were prepared. These films were shown to exhibit k<3.0, as well as low stress, low leakage current density, and high thermal and oxidative stability.

U.S. Pat. No. 6,147,009 of Gill provides an example of a PECVD process using a gas that contains oxygen. In this process, utilizing an organosilicon compound having a ring structure, the precursor gas contains silicon, carbon, nitrogen, and optionally oxygen, and may also be mixed with germanium, nitrogen, and/or fluorine-containing gases. The result is a non-polymeric hydrogenated silicon carbon or non-polymeric hydrogenated oxidized silicon carbon film on a substrate. These films are disclosed to exhibit dielectric constants<4.0, to be thermally stable up to 400° C., and to display low crack propagation in water.

It is also possible to perform chemical vapor deposition at temperatures below 300° C. For example, European Patent No. 1,050,600 of Xia, et al. discloses a thermal CVD process in which a carbon-doped silicon oxide layer is deposited from a process gas of ozone and an organosilane precursor containing at least one Si—C bond. The substrate is heated to less than 250° C. during the deposition, and results in the formation of a material that may be useful as the dielectric layer in integrated circuits.

Another low temperature CVD process is described by Yaue, et al. in U.S. Pat. Nos. 6,054,379 and 6,072,227. The low-k dielectric ($2.5 \leq k \leq 3.0$) material produced by such a process, known as Black Diamond™, is referred to as oxidized organo-silane. The CVD process, which is carried out at temperatures less than 100° C., uses gaseous precursors of an organo-silane and an oxidizer, and is carried out in a low-power capacitively coupled plasma. It is taught that the resulting material has excellent barrier properties.

As noted above, methylhydridosilanes are promising precursors for the chemical vapor deposition of low dielectric constant films which exhibit the properties needed for use in high-volume manufacturing processes. These compounds, also known as methylsilanes, have the general formula $(CH_3)_n SiH_{(4-n)}$, in which n=1–3, and are typically prepared by the reduction of analogous halosilanes such as $(CH_3)_n SiCl_{(4-n)}$, in which n=1–3. Alternatively, trimethylsilane can be prepared via dimethylchlorosilane, a multi-step synthetic route. In both cases, the resulting products typically contain small amounts of chlorides, which can be detrimental to device performance. Specifically, chloride and other mobile ions reduce the electrical properties of the films. In the worse case, at high levels, such impurities can cause current leakage. Therefore, to ensure optimal device performance, it is desirable to remove all traces of chloride from the silane precursors. As a result, there is a need in the art for a process for preparing alkylsilanes such as methylsilane in which chloride content is substantially minimized or eliminated.

BRIEF SUMMARY OF THE INVENTION

The invention includes a process for producing an alkylsilane, comprising reducing an alkoxysilane in the presence of an alkali metal hydride in the presence of a solvent to form an alkylsilane, wherein the alkylsilane has a boiling point lower than a boiling point of the solvent.

The invention also includes a chlorine-free alkylsilane formed from the reduction of an alkoxysilane in the presence of an alkali metal hydride.

DETAILED DESCRIPTION OF THE INVENTION

This invention provides a new route for the synthesis of alkylsilanes that does not involve the use of chloride or other halogen-containing compounds. As a result, there is no detectable chlorine in the resulting products, and the silanes exhibit low levels of other impurities as well. Another advantage to the synthetic route according to the present invention is that in the absence of metal halides, particularly aluminum chloride, rearrangement reactions are less likely to occur. Such rearrangements may lead to the formation of undesirable and/or potentially dangerous silane byproducts. Alkylsilanes made in accordance with the present invention are thus useful for microelectronic applications and minimize or eliminate the negative effects of chloride.

The method of the present invention may also be applicable to the synthesis of arylsilanes. Such a chloride-free synthetic route would be particularly desirable because in the presence of metal halides such as aluminum chloride, rearrangements of arylchlorosilanes can occur, producing undesirable and potentially dangerous silane byproducts.

The process involves the reduction of alkoxysilanes, such as methoxysilane, ethoxysilane and similar compounds, in a high-boiling solvent, preferably diglyme (bis(methoxyethyl) ether) or a similar high-boiling solvent, using lithium aluminum hydride or a similar non chlorine-containing alkali metal hydride. Examples of other alkali metal halides within the scope of the invention are sodium hydride, potassium hydride, and sodium aluminum hydride, though the use of other reducing agents is possible as well. Preferably, the reducing agent is an alkali metal aluminum hydride, and most preferably, is lithium aluminum hydride. As the reduction proceeds, the alkylsilane product is collected, preferably by distillation. The process preferably occurs at temperatures lower than about 90° C., and more preferably at temperatures below about 75° C. However, temperatures above 90° C. may also be used.

As an example, the overall reaction to form methylsilane is shown in Formula I.

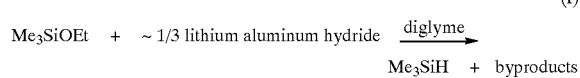

(I)

More specifically, the balanced reaction is:

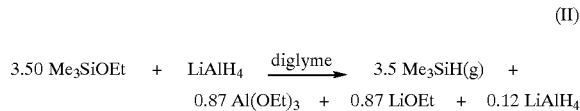

(II)

In the presence of water, the byproducts undergo further reaction as shown in Formula III:

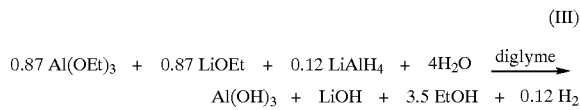

(III)

Generally, the initial byproducts of the reaction are at least one metal alkoxide compound. As shown, for example, in Formula II, the initial byproducts, in addition to unreacted reducing agent, are aluminum ethoxide and lithium alkoxide, which are solids. The ultimate products are generally metal hydroxides (typically solids), hydrogen gas, and an alcohol. In Formula III, for example, the ultimate products are aluminum hydroxide, lithium hydroxide, hydrogen gas and ethanol; ethanol is a liquid that boils at a significantly higher temperature than the desired alkylsilane product. This dramatic difference in boiling points, a difference that is also present between the boiling points of the alkylsilane and the high boiling solvent, makes isolation of the desired product by distillation or other separation technique straightforward. For example, methylsilane boils at 6–7° C., and diglyme, which is the preferred solvent for this reaction, boils at 162° C. Although diglyme is preferred, the use of other solvents is also within the scope of this invention. It is generally preferred to use any ether-based solvent such as, but not limited to, solvents including diethylether and tetrahydrofuran. It is more preferred to utilize an ether-based high boiling solvent such as, for example, butyl ether, and most preferred to use diglyme.

The reduction reaction is preferably performed under an argon atmosphere, but other inert atmospheres such as nitrogen may be used as well. The nature of the inert atmosphere may depend on the particular reactants used. Although lithium aluminum hydride is the most preferred reducing agent, other non-chlorine containing reducing agents are also within the scope of this process. Preferably, the reducing agent is a non-chlorine containing alkali metal hydride. Examples of reducing agents within the scope of the invention are sodium hydride, potassium hydride, and sodium aluminum hydride, although one skilled in the art could vary the reducing agent by experimentation. It is more preferred if the reducing agent is an alkali metal aluminum hydride, and most preferred if the reducing agent is lithium aluminum hydride.

The alkoxysilane used as the starting material may be generally represented by the Formula IV:

(IV)

wherein $R^1$ is generally any branched or linear alkyl group. It is preferred if $R^1$ is a lower alkyl of from 1 to 6 carbon atoms, more preferred if $R^1$ is an alkyl of from 1 to 3 carbon atoms, and most preferred if $R^1$ is methyl or ethyl. For example, preferred groups for $R^1$ include methoxy, ethoxy, n-propoxy and iso-propoxy. $R^2$, $R^3$, and $R^4$ may be the same or different, and may be $R^1$ or H. Examples of some alkoxysilanes within the scope of this invention are methoxysilane, trimethylmethoxysilane, ethoxysilane, trimethylethoxysilane, diethylmethylethoxysilane, diethylmethoxysilane, and mixtures and combinations thereof.

It is also within the scope of this invention to utilize alkoxysilanes in which the silane is substituted with heteroatoms, such as, for example, halogens. However, for the purposes of preparing alkylsilanes to be used for microelectronic applications, it may not be desirable to introduce such heteroatoms into the reaction system, due to the effects of impurities on semiconductor devices which were described previously. Therefore, for these applications, it is preferred if the alkoxysilane is unsubstituted.

Using these precursors, it is possible by the present method to prepare a wide variety of alkylsilanes, which can be generally represented by Formula V:

(V)

wherein $R^2$, $R^3$, and $R^4$ may be the same or different and are generally any branched or linear alkyl group, or H. It is preferred if $R^2$, $R^3$, and $R^4$ are lower alkyls of from 1 to 6 carbon atoms or H, more preferred if $R^2$, $R^3$, and $R^4$ are alkyls of from 1 to 3 carbon atoms or H, and most preferred if $R^2$, $R^3$, and $R^4$ are methyl or ethyl or H. The alkylsilanes which can be prepared by the method of the present invention may be alkylsilanes with one or more substituents the same as one another, such as silane, trimethylsilane, dimethylsilane, and the like, or alkylsilanes containing up to four different substituents, such as methylethylbutylsilane.

In the method according to the present invention, the first step involves the combination of the reducing agent and the high boiling solvent, which are thoroughly mixed. The ratio of the weight of the solvent to the weight of the reducing agent is preferably between about 21 and about 23, and is more preferably about 22. For example, if about 8 kg of reducing agent is to be used, about 173 kg to about 183 kg, and preferably about 189 kg, of solvent are used. After mixing the reducing agent and solvent, the alkoxysilane is preferably slowly added to the reaction vessel, preferably with gentle heating. The ratio of silane to reducing agent is preferably about 3 to about 4, and more preferably is about 3.5.

The alkoxysilane is generally added in at least about two aliquots, during which the formation of the silane product begins and is collected by distillation or other suitable separation technique. The initial aliquot of alkoxysilane is preferably added at a temperature of between about 25° C. and about 65° C., more preferably between about 40° C and about 45° C. The second aliquot, which is preferably added after some of the product has been collected, is preferably added during gentle heating at about 50° C. to about 75° C., and more preferably at about 70° C. to about 75° C. As discussed above, it is preferred if the boiling point of the silane product is lower and more preferably significantly lower (such as about 30° C. lower) than that of the high boiling solvent, and thus is easily isolated from the reaction mixture by distillation or other separation means under ambient pressure. An additional portion of silane product may be collected by further distillation under reduced pressure, such as, for example, at about 200 mm Hg to about 400 mm Hg, with a pot temperature of about 40° C. to about 50° C. The aluminum ethoxide and lithium ethoxide or other similar byproducts, depending on the reactants, and the excess reducing agent may then be further reacted with water in a suitable solvent such as tetrahydrofuran to form, for example, aluminum hydroxide, lithium hydroxide, ethanol, and hydrogen, which are easily disposed of. The selection of the solvent depends on the particular reactants and products.

The invention will be further illustrated in accordance with the following non-limiting examples:

EXAMPLE I

This example demonstrates the formation of trimethylsilane according to the following approximate stoichiometry:

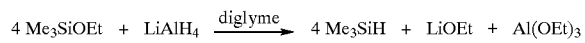

A 22 liter, 4-necked flask equipped with a mechanical stirrer, pot thermometer, addition funnel, and a dry ice-cooled distillation head with a short column was charged with 5L of diglyme and 189.75 g (5 mol) of lithium aluminum hydride. After stirring for 30 minutes, 1182.5 g (10 mol) of trimethylethoxysilane was added at a temperature range between 25° C. and 62° C. over 3 hours. Collection of the trimethylsilane product by distillation at a head temperature of 6° C. to 8° C. was begun at this time. The remainder of the trimethylethoxysilane (886.9 g, 7.5 mol) was then added at a temperature range of between 50° C. and 70° C. over 2.5 hours with heating. After addition of the trimethylethoxysilane was complete, the reaction mixture was heated at a temperature range of between 50° C. and 70° C. for an additional 2 hours. By this time, 1.07 kg of trimethylsilane had been collected. Another portion of trimethylsilane was isolated by applying a slight vacuum (400 mm Hg) at a pot temperature range of between 40° C. and 50° C. A total of 1.19 kg (91.64% yield) of trimethylsilane was obtained, for which the purity was determined to be 99.96%.

EXAMPLE II

A one liter, 3-neck flask equipped with a magnetic stirrer, pot thermometer, addition funnel, and a short column leading to a dry ice condenser connected to a receiver was charged with 250 ml diglyme and then 12.65 g lithium aluminum hydride. After stirring for 15 minutes, one third of the total amount of trimethylethoxysilane (118.25 g) added at 30° to 40° C. pot temperature. The mixture was then slowly heated to 65° to 75° C. and held at that temperature for 15–30 minutes. The remainder of the trimethylethoxysilane was then added at the same temperature and trimethylsilane was gradually collected at a temperature range between 7 and 10° C. After condensation and agitation, the mixture was distilled at 65° C. to 85° C. for 2 hours. 47.8 g of trimethylsilane was collected. Another 13 g was isolated by applying slight vacuum (below 7° C. at 200 mmHg, pot temperature of 50° C). The yield was calculated to be 62/74.20×100%=84%. The GC indicated that the product was 100% trimethylsilane, and had no detectable chloride.

This invention fulfills a need in the art for a straightforward, low temperature synthesis of alkylsilanes that are chloride-free such that they are attractive precursors for various CVD methods to result in materials useful for microelectronic applications. The process may be used to form triethylsilane, dimethylsilane and methyl silane, as well as other alkylsilane reduction reaction products of alkoxysilanes in high boiling solvents using a reducing agent such as an alkali metal hydride at the temperatures noted above. The resulting compounds, which are obtained in high yield and at extremely high purity, are useful for microelectronic applications including the production of low dielectric constant interlayer materials which can be produced, for example, by chemical vapor deposition (CVD) methods.

It will be appreciated by those skilled in the art that changes could be made to the embodiments described above without departing from the broad inventive concept thereof It is understood, therefore, that this invention is not limited to the particular embodiments disclosed, but it is intended to cover modifications within the spirit and scope of the present invention as defined by the appended claims.

We claim:

1. A process for producing an alkylsilane, comprising reducing an alkoxysilane in the presence of an alkali metal hydride in the presence of a solvent to form an alkylsilane, wherein the alkylsilane has a boiling point lower than a boiling point of the solvent.

2. The process according to claim 1, wherein the alkylsilane is chloride free.

3. The process according to claim 1, wherein the alkoxysilane has formula IV:

wherein $R^1$ is selected from the group consisting of linear or branched alkyls; and $R^2$, $R^3$, and $R^4$ are each independently selected from the group consisting of $R^1$ and H.

4. The process according to claim 3, wherein $R^1$ is selected from the group consisting of linear or branched lower alkyls of from 1 to 6 carbon atoms, and $R^2$, $R^3$, and $R^4$ are each independently selected from the group consisting $R^1$ and H.

5. The process according to claim 4, wherein $R^1$ is selected from the group consisting of methyl and ethyl, and $R^2$, $R^3$, and $R^4$ are each independently selected from the group consisting of $R^1$ and H.

6. The process according to claim 3, wherein the alkoxysilane is selected from the group consisting of methoxysilane, trimethylmethoxysilane, ethoxysilane, trimethylethoxysilane, diethylmethylethoxysilane, dimethylethylethoxysilane, diethylmethoxysilane, dimethylmethoxysilane, dimethylethoxysilane, and mixtures and combinations thereof.

7. The process according to claim 1, wherein the alkali metal hydride is an alkali metal aluminum hydride.

8. The process according to claim 7, wherein the alkali metal hydride is lithium aluminum hydride.

9. The process according to claim 1, wherein the reduction reaction occurs at a temperature no greater than about 90° C.

10. The process according to claim 9, wherein the reduction reaction occurs at a temperature no greater than about 75° C.

11. The process according to claim 1, wherein the solvent is a high-boiling ether based-solvent.

12. The process according to claim 11, wherein the solvent is diglyme.

13. The process according to claim 1, wherein the alkylsilane is trimethylsilane.

14. A chlorine-free alkylsilane formed from the reduction of an alkoxysilane in the presence of an alkali metal hydride.

15. A chloride-free alkylsilane formed from the reduction of an alkoxysilane in the presence of an alkali metal hydride, wherein the alkylsilane has the formula V:

$$(R^2R^3R^4)-Si-H \qquad (V)$$

wherein $R^2$, $R^3$, $R^4$ are each independently selected from the group consisting of H and linear or branched alkyl groups.

* * * * *